| United States Patent [19] | [11] 4,118,574 |
|---|---|
| Beck et al. | [45] Oct. 3, 1978 |

[54] HERBICIDAL 1,4-DIPHENYL-3-PYRAZOLIN-5-ONES

[75] Inventors: James Richard Beck; Robert Peter Gajewski, both of Indianapolis, Ind.

[73] Assignee: Eli Lilly and Company, Indianapolis, Ind.

[21] Appl. No.: 850,323

[22] Filed: Nov. 10, 1977

Related U.S. Application Data

[60] Division of Ser. No. 724,502, Sep. 20, 1976, Pat. No. 4,075,033, which is a continuation-in-part of Ser. No. 639,744, Dec. 11, 1975, abandoned.

[51] Int. Cl.² .......................... C07D 231/22
[52] U.S. Cl. .................................... 548/363
[58] Field of Search ............... 548/363; 71/92

[56] References Cited

U.S. PATENT DOCUMENTS

| 2,844,510 | 7/1956 | Lorenz et al. | 424/200 |
|---|---|---|---|
| 3,087,933 | 4/1963 | Matter et al. | 548/360 |
| 3,092,483 | 6/1963 | Perkow | 71/92 |
| 3,133,079 | 3/1964 | Luckenbaugh | 71/92 |
| 3,166,568 | 1/1965 | Nicolaus et al. | 548/363 |
| 3,644,355 | 2/1972 | Ehnev et al. | 260/250 A |
| 3,823,135 | 7/1974 | Pilgram et al. | 260/251 R |
| 3,867,403 | 2/1975 | Feeny | 71/92 |
| 3,922,161 | 11/1975 | Walworth et al. | 71/92 |
| 4,013,441 | 3/1977 | Bianchetti et al. | 71/92 |

OTHER PUBLICATIONS

Belkh, Ber., 1898, vol. 31, pp. 3160–3164.
Knorr et al., Ber., 1887, vol. 20, pp. 2545–2550.
Merck Index, 8th Ed., 1968, p. 93.
Herbicide Handbook, 1974, pp. 241–246.
Windisch, Chem. Abst. 1960, vol. 54, No. 17423g.
Herrmann et al., Chem. Abst. 1959, vol. 53, 4305b.
Veibel et al., Acta Chem. Scand. 1954, vol. 8, pp. 768–776.
Beilsteins Handbuch der Organischen Chemie, 4th Ed., 1936, vol. 24 (to 1910), pp. 150–151, Berlin, Springer.
Beilsteins Handbuch der Organischen Chemie, 4th Ed., 1954, vol. 24, 2nd Suppl. (1920–1929), p. 73, Berlin, Springer.

*Primary Examiner*—Natalie Trousof
*Assistant Examiner*—Natalia Harkaway
*Attorney, Agent, or Firm*—Dwight E. Morrison; Arthur R. Whale

[57] ABSTRACT

A class of 1,4-diphenyl-3-pyrazolin-5-ones are useful as herbicides. The compounds have small alkyl substituents at the 2-position, and the phenyl rings may be substituted as well.

11 Claims, No Drawings

HERBICIDAL 1,4-DIPHENYL-3-PYRAZOLIN-5-ONES

This is a division of Ser. No. 724,502 filed Sept. 20, 1976 now U.S. Pat. No. 4,075,033 which is a continuation-in-part of Ser. No. 639,744 filed Dec. 11, 1975 now abandoned.

BACKGROUND OF THE INVENTION

This invention belongs to the field of agricultural chemistry, and provides new herbicidal compounds to the art. The growth of weeds, which are often defined as plants growing where they are not wanted, has well-known deleterious effects on crops which are infested with such plants. Unwanted plants growing in cropland, as well as in fallow land, consume soil nutrients and water, and compete with crop plants for sunlight. Thus, weed plants constitute a drain on the soil and cause measurable losses in the yield of crops.

The compounds of this invention are new to organic chemistry. Some compounds which have a relationship to the present invention, however, are known in the herbicidal art. Earlier workers have found herbicides among the pyridazinones, for example, U.S. Pat. No. 3,644,355. Some pyrimidinone herbicides have also been disclosed in the agricultural chemical art, such as the 6-alkyl-2,5-dihalo-3-phenyl-4-pyrimidinones of U.S. Pat. No. 3,823,135.

Some diphenyl-5-pyrazolinones have been disclosed, for example, the 3-methyl-1,4-diphenyl compound of Beckh, Ber. 31, 3164 (1898) and the 2-methyl-1,3-diphenyl compound of Knorr et al., Ber. 20, 2549 (1887). A pharmaceutical pyrazolinone is 2,3-dimethyl-1-phenyl-3-pyrazolin-5-one, called antipyrine, which was formerly used as an analgesic. Merck Index, 93 (8th ed. 1968).

SUMMARY OF THE INVENTION

This invention provides to the agricultural chemical art new compounds of the formula

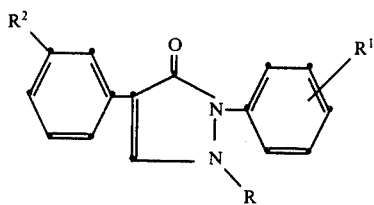

wherein
R represents $C_1-C_3$ alkyl;
$R^1$ and $R^2$ independently represent hydrogen, chloro, fluoro, bromo, methyl or trifluoromethyl, provided that $R^1$ and $R^2$ do not simultaneously represent hydrogen; provided that $R^1$ may not be bromo or chloro in the 4-position.

The invention also provides new herbicidal compositions, and methods of reducing the vigor of unwanted herbaceous plants, which make use of the compounds above.

DESCRIPTION OF THE PREFERRED EMBODIMENT

In the above formula, the term $C_1-C_3$ alkyl refers to methyl, ethyl, or propyl.

The formula above is believed to describe the invention clearly. In order to assure that agricultural chemists understand the invention, however, the following exemplary compounds are presented. It will be understood that the compounds below do not bound the invention, but are merely typical of it.

4-(3-bromophenyl)-2-methyl-1-phenyl-3-pyrazolin-5-one
1-(3-chlorophenyl)-2-ethyl-4-(3-fluorophenyl)-3-pyrazolin-5-one
4-(3-chlorophenyl)-1-(2-fluorophenyl)-2-propyl-3-pyrazolin-5-one
1,4-bis(3-bromophenyl)-2-methyl-3-pyrazolin-5-one
2-propyl-1,4-bis(m-tolyl)-3-pyrazolin-5-one
4-(3-chlorophenyl)-2-methyl-1-(α,α,α-trifluoro-p-tolyl)-3-pyrazolin-5-one
2-ethyl-1-phenyl-4-(m-tolyl)-3-pyrazolin-5-one
1-(3-chlorophenyl)-2-methyl-4-(m-tolyl)-3-pyrazolin-5-one
1-(2-bromophenyl)-2-propyl-4-(α,α,α-trifluoro-m-tolyl)-3-pyrazolin-5-one
4-(3-chlorophenyl)-2-methyl-1-(o-tolyl)-3-pyrazolin-5-one
4-(3-bromophenyl)-1-(2-chlorophenyl)-2-methyl-3-pyrazolin-5-one
2-ethyl-1,4-bis(α,α,α-trifluoro-m-tolyl)-3-pyrazolin-5-one
1-(3-fluorophenyl)-2-methyl-4-(α,α,α-trifluoro-m-tolyl)-3-pyrazolin-5-one
2-ethyl-1-(2-fluorophenyl)-4-(3-fluorophenyl)-3-pyrazolin-5-one
2-ethyl-1-(3-fluorophenyl)-4-(m-tolyl)-3-pyrazolin-5-one
4-(3-bromophenyl)-1-(4-fluorophenyl)-2-propyl-3-pyrazolin-5-one
1-(2-bromophenyl)-4-(3-fluorophenyl)-2-propyl-3-pyrazolin-5-one
1-(3-bromophenyl)-2-methyl-4-(m-tolyl)-3-pyrazolin-5-one
2-methyl-4-(m-tolyl)-1-(α,α,α-trifluoro-o-tolyl)-3-pyrazolin-5-one
4-(3-fluorophenyl)-2-methyl-1-(α,α,α-trifluoro-m-tolyl)-3-pyrazolin-5-one The preferred compounds of this invention are those of the structural formula above
wherein R represents $C_1-C_2$ alkyl;
$R^1$ represents hydrogen, chloro, or fluoro; provided that $R^1$ may not be chloro in the 4-position; and
$R^2$ represents trifluoromethyl.

Such preferred compounds are more particularly identified as the following:
2-methyl-1-phenyl-4-(α,α,α-trifluoro-m-tolyl)-3-pyrazolin-5-one, 2-ethyl-1-phenyl-4-(α,α,α-trifluoro-m-tolyl)-3-pyrazolin-5-one, 2-ethyl-1-(4-fluorophenyl)-4-(α,α,α-trifluoro-m-tolyl)-3-pyrazolin-5-one, 2-ethyl-1-(3-chlorophenyl)-4-(α,α,α-trifluoro-m-tolyl)-3-pyrazolin-5-one, 2-methyl-1-(3-chlorophenyl)-4-(α,α,α-trifluoro-m-tolyl)-3-pyrazolin-5-one, 2-methyl-1-(2-chlorophenyl)-4-(α,α,α-trifluoro-m-tolyl)-3-pyrazolin-5-one, 1-(3-bromophenyl)-2-ethyl-4-(α,α,α-trifluoro-m-tolyl)-3-pyrazolin-5-one, 1,4-bis(3-chlorophenyl)-2-ethyl-3-pyrazolin-5-one, and 2-methyl-1-(4-fluorophenyl)-4-(α,α,α-trifluoro-m-tolyl)-3-pyrazolin-5-one.

The compounds of this invention are made most advantageously by a 3-step process. First, a methyl or ethyl ester of phenylacetic acid, bearing the $R^2$ substituent on the phenyl ring, is reacted with di(Alk)formamide di(Alk) acetal neat or in dimethylformamide to produce an intermediate substituted ester of atropic acid of the formula (I) below.

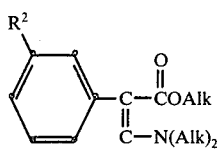

The term Alk refers to methyl or ethyl. The reaction is carried out at temperatures from about 80° to about 140° C. in a flask open to the atmosphere.

The intermediate I is then reacted with a phenylhydrazine or a hydrohalide thereof, bearing the $R^1$ substituent, if any, on its phenyl ring, to form the desired product, lacking the 2-alkyl group. When a phenylhydrazine in the free base form is used, the reaction is carried out in an aprotic solvent. The aromatic solvents such as benzene and toluene, the aliphatics such as hexane and octane, and the halogenated solvents such as methylene chloride and chloroform are appropriate solvents. Xylenes are the preferred solvents. The most convenient reaction temperature is the reflux temperature of the reaction mixture, but other temperatures from room temperature to about 120° C. can be used if convenient in a given instance.

When a phenylhydrazine hydrohalide is used, the reaction can be carried out in an aprotic solvent as described above in the presence of a base. Tertiary organic amines such as triethylamine, pyridine, triethanolamine and the like, and inorganic bases such as potassium carbonate, sodium bicarbonate, alkali metal hydroxides and the like are satisfactory bases.

Alternatively, reactions using phenylhydrazine hydrohalides may be performed by first reacting the hydrazine with the intermediate I in a lower alkanol at the reflux temperature of the mixture to exchange the di(Alk)amino group of I with the arylhydrazine moiety. The resulting intermediate may then be cyclized by heating in an aprotic solvent such as xylene at temperatures from about 50° to about 120° C. Alternatively, the resulting intermediate may be cyclized by heating in a lower alkanol at reflux temperature with inorganic bases such as potassium carbonate, alkali metal hydroxides, or alkali metal alkoxides.

The 2-substituent is easily added by alkylation with, for example, an alkyl iodide in the presence of a strong inorganic base. It is also possible to alkylate at the 2-position with a dialkyl sulfate under strong basic conditions. Again, the most convenient reaction temperature for the alkylation is the reflux temperature of the reaction mixture, as is commonly done in such reactions. Alkylations of this type are frequently performed and are common in the chemical literature.

All of the starting compounds used in synthesizing the pyrazolinones are commonly known in the chemical art and are readily obtainable.

A few typical preparative examples will be shown to assure that organic chemists can obtain any desired compound of this invention. All of the products described below were identified by nuclear magnetic resonance analysis and elemental microanalysis.

EXAMPLE 1

2-methyl-1-phenyl-4-(α,α,α-trifluoro-m-tolyl)-3-pyrazolin-5-one

A 10.9 g. portion of 3-trifluoromethylphenylacetic acid, methyl ester, was combined with 11.9 g. of dimethylformamide dimethyl acetal and the mixture was heated overnight on the steam bath. In the morning, the reaction mixture was taken up in methanol and poured over ice. The aqueous mixture was filtered, and the solids were recrystallized from aqueous ethanol to produce 4 g. of m-trifluoromethyl-β-(dimethylamino)atropic acid, methyl ester, m.p. 45°–49° C.

The ester prepared above was combined with 1.6 g. of phenylhydrazine in 25 ml. of benzene and the mixture was refluxed overnight. About 25 ml. of p-xylene was added and the mixture was refluxed for 2 hours more. The reaction mixture was then cooled, and the resulting solids were separated by filtration and identified as 2.6 g. of 1-phenyl-4-(α,α,α-trifluoro-m-tolyl)-3-pyrazolin-5-one.

A 1.5 g. portion of the pyrazolinone was dissolved in 50 ml. of methanol, and 0.7 g. of methyl iodide and 0.7 g. of potassium carbonate were added. The mixture was stirred at reflux temperature overnight. The mixture was then poured over ice, and the aqueous mixture was filtered to recover the product, which was recrystallized from ethyl acetate-hexane. The product was 0.85 g. of 2-methyl-1-phenyl-4-(α,α,α-trifluoro-m-tolyl)-3-pyrazolin-5-one, m.p. 153°–155° C.

|   | Theoretical | Found |
|---|---|---|
| C | 64.15% | 64.17% |
| H | 4.12 | 4.19 |
| N | 8.80 | 8.77 |

EXAMPLE 2

2-methyl-1-phenyl-4-(3-fluorophenyl)-3-pyrazolin-5-one

A 9 g. portion of 3-fluorophenylacetic acid, methyl ester, was reacted with 6.5 g. of dimethylformamide dimethyl acetal in 15 ml. of dimethylformamide at 120° C. to produce 11.2 g. of the corresponding m-fluoroatropic acid, methyl ester. The ester was reacted with 5.4 g. of phenylhydrazine in 50 ml. of toluene at reflux temperature for 4 hours. An equal volume of m-xylene was then added, and the mixture was refluxed overnight. The mixture was then cooled and decanted, and the solids were triturated with benzene and filtered. The separated solids were slurried in hot benzene-ethyl acetate, and filtered again. The solids were then recrystallized from ethanol to produce 2.9 g. of 1-phenyl-4-(3-fluorophenyl)-3-pyrazolin-5-one, m.p. 189° C.

A 2.4 g. portion of the above pyrazolinone was combined with 3.9 g. of methyl iodide and reacted as described in Example 1 above. The product, after recrystallization from benzene-hexane, was 1.5 g. of 2-methyl-1-phenyl-4-(3-fluorophenyl)-3-pyrazolin-5-one, m.p. 134° C.

|   | Theoretical | Found |
|---|---|---|
| C | 71.63% | 71.35% |
| H | 4.88 | 5.01 |
| N | 10.44 | 10.17 |

EXAMPLE 3

1-phenyl-2-propyl-4-(α,α,α-trifluoro-m-tolyl)-3-pyrazolin-5-one

A 3 g. portion of the 2-unsubstituted pyrazolinone of Example 1 was reacted with 10 ml. of propyl iodide to produce 0.45 g. of 1-phenyl-2-propyl-4-(α,α,α-trifluoro-m-tolyl)-3-pyrazolin-5-one, an oily liquid.

|   | Theoretical | Found |
|---|---|---|
| C | 65.89% | 65.64% |
| H | 4.95 | 5.09 |
| N | 8.09 | 7.97 |

EXAMPLE 4

2-ethyl-1-phenyl-4-(α,α,α-trifluoro-m-tolyl)-3-pyrazolin-5-one

A 2.5 g. portion of the 2-unsubstituted pyrazolinone of Example 1 was reacted with 1.2 g. of ethyl iodide. The alkylated product was 1.2 g. of 2-ethyl-1-phenyl-4-(α,α,α-trifluoro-m-tolyl)-3-pyrazolin-5-one, m.p. 156°–157° C.

|   | Theoretical | Found |
|---|---|---|
| C | 65.06% | 65.25% |
| H | 4.55 | 4.65 |
| N | 8.43 | 8.40 |

EXAMPLE 5

2-methyl-1-phenyl-4-(3-chlorophenyl)-3-pyrazolin-5-one

A 17 g. portion of 3-chlorophenylacetic acid, methyl ester, was combined with 12 g. of dimethylformamide dimethyl acetal in 100 ml. of dimethylformamide and the mixture was heated in an open flask at the boiling temperature of the mixture for 6 hours. The hot reaction mixture was then poured over ice, and the aqueous mixture was filtered. The solids were recrystallized from benzenehexane to produce 13 g. of the 3-chloroatropic acid, methyl ester, m.p. 84°–86° C.

A 4.8 g. portion of the above intermediate was reacted with 2.2 g. of phenylhydrazine to produce 3.5 g. of 1-phenyl-4-(3-chlorophenyl)-3-pyrazolin-5-one, m.p. 197°–199° C.

A 2 g. portion of the above intermediate was alkylated with 2.7 g. of methyl iodide to produce 1 g. of 2-methyl-1-phenyl-4-(3-chlorophenyl)-3-pyrazolin-5-one, m.p. 149°–150° C.

|   | Theoretical | Found |
|---|---|---|
| C | 67.49% | 67.24% |
| H | 4.60 | 4.38 |
| N | 9.84 | 9.80 |

EXAMPLE 6

2-methyl-1-(4-fluorophenyl)-4-(α,α,α-trifluoro-m-tolyl)-3-pyrazolin-5-one

A 5.5 g. portion of the atropic ester of Example 1 was combined with 3.5 g. of 4-fluorophenylhydrazine hydrochloride and 2 g. of triethylamine in 50 ml. of benzene. The mixture was stirred at reflux temperature for 5 hours, after which about half of the benzene was allowed to evaporate and an equivalent amount of m-xylene was added. The mixture was then stirred at reflux overnight, and the reaction mixture was evaporated to dryness under vacuum. The residue was partitioned between ethyl acetate and water, and the organic layer was dried over sodium sulfate and evaporated to dryness. The residue was chromatographed on silica gel with ethyl acetate as the eluant. The product-containing fractions were combined and evaporated to dryness to produce about 3.5 g. of crude product, which was recrystallized from methanol to produce 2.7 g. of purified 1-(4-fluorophenyl)-4-(α,α,α-trifluoro-m-tolyl)-3-pyrazolin-5-one, m.p. 171°–173° C.

Two g. of the above intermediate was alkylated with 2.7 g. of methyl iodide to produce 1.6 g. of 2-methyl-1-(4-fluorophenyl)-4-(α,α,α-trifluoro-m-tolyl)-3-pyrazolin-5-one, m.p. 165° C.

|   | Theoretical | Found |
|---|---|---|
| C | 60.72% | 60.99% |
| H | 3.60 | 3.58 |
| N | 8.33 | 8.32 |

EXAMPLE 7

2-methyl-1-(3-chlorophenyl)-4-(α,α,α-trifluoro-m-tolyl)-3-pyrazolin-5-one

A 3.5 g. portion of the atropic ester of Example 1 was reacted with 2.3 g. of 3-chlorophenylhydrazine hydrochloride in the presence of 1.3 g. of triethylamine in m-xylene according to the scheme of Example 6. The product was 2 g. of 1-(3-chlorophenyl)-4-(α,α,α-trifluoro-m-tolyl)-3-pyrazolin-5-one, m.p. 182°–184° C.

A 1.65 g. portion of the above intermediate was alkylated with 2 g. of methyl iodide to produce 1 g. of 2-methyl-1-(3-chlorophenyl)-4-(α,α,α-trifluoro-m-tolyl)-3-pyrazolin-5-one, m.p. 130°–131° C.

|   | Theoretical | Found |
|---|---|---|
| C | 57.89% | 58.13% |
| H | 3.43 | 3.59 |
| N | 7.94 | 8.04 |

EXAMPLE 8

2-methyl-1-(m-tolyl)-4-(α,α,α-trifluoro-m-tolyl)-3-pyrazolin-5-one

A 2.2 g. portion of the atropic ester of Example 1 was reacted with 1.3 g. of m-tolylhydrazine hydrochloride in the presence of triethylamine to produce 1.7 g. of 1-(m-tolyl)-4-(α,α,α-trifluoro-m-tolyl)-3-pyrazolin-5-one, m.p. 158°–159° C.

A 1.6 g. portion of the above intermediate was alkylated with 2 g. of methyl iodide to produce 1 g. of 2-methyl-1-(m-tolyl)-4-(α,α,α-trifluoro-m-tolyl)-3-pyrazolin-5-one, m.p. 153°–154° C.

|   | Theoretical | Found |
|---|---|---|
| C | 65.06% | 65.19% |
| H | 4.55 | 4.32 |
| N | 8.43 | 8.33 |

EXAMPLE 9

2-methyl-1,4-bis(α,α,α-trifluoro-m-tolyl)-3-pyrazolin-5-one

A 3.5 g. portion of the atropic ester of Example 1 was reacted with 2.7 g. of α,α,α-trifluoro-m-tolylhydrazine hydrochloride in the presence of triethylamine to produce 2.4 g. of 1,4-bis(α,α,α-trifluoro-m-tolyl)-3-pyrazolin-5-one, m.p. 207°–208° C.

A 1.8 g. portion of the above pyrazolinone was reacted with 2 g. of methyl iodide to produce 1.25 g. of 2-methyl-1,4-bis(α,α,α-trifluoro-m-tolyl)-3-pyrazolin-5-one, m.p. 110°–111° C.

|   | Theoretical | Found |
|---|---|---|
| C | 56.26% | 56.04% |
| H | 2.62 | 2.86 |
| N | 7.29 | 7.19 |

EXAMPLE 10

2-methyl-1-(2-chlorophenyl)-4-(α,α,α-trifluoro-m-tolyl)-3-pyrazolin-5-one

A 2.7 g. portion of the atropic ester of Example 1 was reacted with 1.8 g. of 2-chlorophenylhydrazine hydrochloride in the presence of triethylamine to produce 1 g. of 1-(2-chlorophenyl)-4-(α,α,α-trifluoro-m-tolyl)-3-pyrazolin-5-one, m.p. 236° C.

One g. of the above pyrazolinone was alkylated with 1 g. of methyl iodide to produce 0.45 g. of 2-methyl-1-(2-chlorophenyl)-4-(α,α,α-trifluoro-m-tolyl)-3-pyrazolin-5-one, m.p. 175° C.

|   | Theoretical | Found |
|---|---|---|
| C | 57.87% | 57.39% |
| H | 3.40 | 3.51 |
| N | 7.94 | 7.93 |

EXAMPLE 11

2-ethyl-1-(3-chlorophenyl)-4-(α,α,α-trifluoro-m-tolyl)-3-pyrazolin-5-one

A 2.6 g. portion of 1-(3-chlorophenyl)-4-(α,α,α-trifluoro-m-tolyl)-3-pyrazolin-5-one, prepared in Example 7, was alkylated with ethyl iodide to produce 0.25 g. of 2-ethyl-1-(3-chlorophenyl)-4-(α,α,α-trifluoro-m-tolyl)-3-pyrazolin-5-one, an oily liquid.

|   | Theoretical | Found |
|---|---|---|
| C | 58.95% | 58.89% |
| H | 3.85 | 3.61 |
| N | 7.64 | 7.52 |

EXAMPLE 12

2-ethyl-1-(3-fluorophenyl)-4-(α,α,α-trifluoro-m-tolyl)-3-pyrazolin-5-one

A 15 g. portion of the atropic ester of Example 1 was allowed to react with 10 g. of 3-fluorophenylhydrazine hydrochloride in methanol at reflux temperature for about 2 days. The solvent was evaporated and the residue partitioned between ethyl acetate and water. The organic layer was separated and concentrated in vacuo to leave a residue. The residue was recrystallized from a mixture of ethyl acetate and hexane to yield product having a melting point of about 172° C. and weighing 2.1 g. The product was identified as 1-(3-fluorophenyl)-4-(α,α,α-trifluoro-m-tolyl)-3-pyrazolin-5-one.

The 2.1 g. of pyrazolinone prepared above was placed in 40 ml. of ethanol together with 15 ml. of ethyl iodide and 1 g. of potassium carbonate and the mixture refluxed for about 8 hours. The reaction product mixture was concentrated in vacuo and the residue partitioned between ethyl acetate and water. The ethyl acetate layer was separated and dried, and concentrated in vacuo, and the residue chromatographed on a silica gel column using a mixture of ethyl acetate and hexane in a ratio of 1:2. The product which was isolated had a melting point of about 140-141° C. and weighed 0.7 g. The product was identified as 2-ethyl-1-(3-fluorophenyl)-4-(α,α,α-trifluoro-m-tolyl)-3-pyrazolin-5-one.

|   | Theoretical | Found |
|---|---|---|
| C | 61.71% | 61.72% |
| H | 4.00 | 4.06 |
| N | 8.00 | 8.00 |

EXAMPLE 13

2-ethyl-1,4-bis(α,α,α-trifluoro-m-tolyl)-3-pyrazolin-5-one

A 4 g. portion of 1,4-bis(α,α,α-trifluoro-m-tolyl)-3-pyrazolin-5-one (from Example 9) was heated with 20 ml. of ethyl iodide, 3 g. of potassium carbonate, and 40 ml. of ethanol at reflux temperature for about 4 hours. The reaction product mixture was concentrated in vacuo and extracted with ethyl acetate. The extract was dried over anhydrous magnesium sulfate, the drying agent filtered off and the filtrate concentrated in vacuo. On standing overnight the residue solidified and was recrystallized from a mixture of hexane and benzene. The solid was chromatographed on a silica gel column using a mixture of ethyl acetate and hexane in the ratio of 1:2. The product from the column was then recrystallized from a mixture of hexane and benzene to yield product having a melting point of about 110°–111° C., and identified as 2-ethyl-1,4-bis(α,α,α-trifluoro-m-tolyl)-3-pyrazolin-5-one.

|   | Theoretical | Found |
|---|---|---|
| C | 57.00% | 56.63% |
| H | 3.50 | 3.49 |
| N | 7.00 | 6.85 |

EXAMPLE 14

1-(3-bromophenyl)-2-ethyl-4-(α,α,α-trifluoro-m-tolyl)-3-pyrazolin-5-one

A 13.7 g. portion of the atropic ester of Example 1 was allowed to react with 11.2 g. of 3-bromophenylhydrazine hydrochloride in 100 ml. of methanol at reflux temperature overnight. The solvent was evaporated, and the residue was refluxed in 100 ml. of m-xylene and 5 g. of triethylamine for about 16 hours. The reaction mixture was concentrated in vacuo and the residue chromatographed on a silica gel column using 1:1 ethyl acetate-hexane. There was obtained 7.5 g. of product, which was identified as 1-(3-bromophenyl)-4-(α,α,α-trifluoro-m-tolyl)-3-pyrazolin-5-one.

A 7.5 g. portion of the above pyrazolinone was combined with 4 g. of potassium carbonate and 15 ml. of ethyl iodide in 100 ml. of ethanol and heated in the same manner as previously described for other similar compounds. There was obtained 2.0 g. of product having a melting point of about 106° C., and identified as 1-(3-bromophenyl)-2-ethyl-4-($\alpha,\alpha,\alpha$-trifluoro-m-tolyl)-3-pyrazolin-5-one.

|   | Theoretical | Found |
|---|---|---|
| C | 52.57% | 52.80% |
| H | 3.43 | 3.49 |
| N | 6.81 | 6.98 |

EXAMPLE 15

2-ethyl-1-(4-fluorophenyl)-4-($\alpha,\alpha,\alpha$-trifluoro-m-tolyl)-3-pyrazolin-5-one A 6 g. portion of 1-(4-fluorophenyl)-4-($\alpha,\alpha,\alpha$-trifluoro-m-tolyl)-3-pyrazolin-5-one (prepared in Example 6) was mixed with 4 g. of potassium carbonate and 15 ml. of ethyl iodide in 100 ml. of ethanol and refluxed overnight. There was isolated in the usual manner 1.8 g. of product having a melting point of about 92° C., and identified as 2-ethyl-1-(4-fluorophenyl)-4-($\alpha,\alpha,\alpha$-trifluoro-m-tolyl)-3-pyrazolin-5-one.

|   | Theoretical | Found |
|---|---|---|
| C | 61.72% | 61.87% |
| H | 4.03 | 4.20 |
| N | 8.00 | 8.06 |

EXAMPLE 16

1,4-bis(3-chlorophenyl)-2-ethyl-3-pyrazolin-5-one

A 12 g. portion of the 3-chloroatropic acid, methyl ester (prepared in Example 5 above) was allowed to react with 10 g. of 3-chlorophenylhydrazine hydrochloride in 100 ml. of methanol at reflux temperature overnight. There was obtained 10 g. of product having a melting point of about 173°–174° C., and identified as 1,4-bis(3-chlorophenyl)-3-pyrazolin-5-one.

A mixture of 7 g. of the pyrazolinone prepared above, 4 g. of potassium carbonate, and 15 ml. of ethyl iodide in ethanol was refluxed overnight. There was isolated, after recrystallization from ether, 3.0 g. of product having a melting point of about 101° C., and identified as 1,4-bis(3-chlorophenyl)-2-ethyl-3-pyrazolin-5-one.

|   | Theoretical | Found |
|---|---|---|
| C | 61.28% | 61.04% |
| H | 4.24 | 4.21 |
| N | 8.41 | 8.55 |

EXAMPLE 17

4-(3-chlorophenyl)-2-ethyl-1-($\alpha,\alpha,\alpha$-trifluoro-m-tolyl)-3-pyrazolin-5-one A mixture of 12 g. of the 3-chloroatropic acid, methyl ester (prepared in Example 5 above), 13 g. of m-trifluoromethylphenylhydrazine hydrochloride and 100 ml. of methanol was refluxed overnight to yield 4.6 g. of product having a melting point of about 190°–192° C., and identified as 4-(3-chlorophenyl)-1-($\alpha,\alpha,\alpha$-trifluoro-m-tolyl)-3-pyrazolin-5-one.

A mixture of 4.6 g. of the pyrazolinone prepared above, 4 g. of potassium carbonate, 15 ml. of ethyl iodide and 50 ml. of ethanol was refluxed overnight. The reaction product mixture was worked up in the customary way to yield 1.8 g. of product having a melting point of about 113°–114° C. and identified as 4-(3-chlorophenyl)-2-ethyl-1-($\alpha,\alpha,\alpha$-trifluoro-m-tolyl)-3-pyrazolin-5-one.

|   | Theoretical | Found |
|---|---|---|
| C | 58.95% | 58.84% |
| H | 3.85 | 3.89 |
| N | 7.64 | 7.63 |

EXAMPLE 18

1-(3-chlorophenyl)-2-ethyl-4-phenyl-3-pyrazolin-5-one

A 120 g. portion of phenylacetic acid, methyl ester, was combined with 95 g. of dimethylformamide dimethyl acetal in 200 ml. of dimethylformamide, and heated to gentle reflux for about four days, while adding, at intervals, 5 g. portions of dimethylformamide until a total of 140 g. additional had been added. At the end of the heating period, the reaction mixture was allowed to cool to room temperature and was poured over crushed ice. The oily product which separated eventually crystallized. The crystalline product was washed with water, cooled in the refrigerator, filtered off and air dried. The crude product was recrystallized from cyclohexane to yield product having a melting point of about 58°–60° C., which was identified as $\beta$-(dimethylamino)atropic acid, methyl ester.

|   | Theoretical | Found |
|---|---|---|
| C | 70.22% | 70.47% |
| H | 7.37 | 7.36 |
| N | 6.82 | 6.85 |

A mixture of 10.5 g. of the atropic acid, methyl ester, 9.1 g. of 3-chlorophenylhydrazine hydrochloride, and 200 ml. of methanol was refluxed overnight. The reaction product mixture was worked up in the usual manner to yield 11 g. of crude 1-(3-chlorophenyl)-4-phenyl-3-pyrazolin-5-one. A sample recrystallized from methanol had a melting point of about 211°–212° C.

A mixture of 4 g. of the above prepared pyrazolinone, 20 ml. of ethyl iodide, 20 ml. of ethyl bromide, 3 g. of potassium carbonate, and 40 ml. of ethanol was refluxed for about 4 hours. The reaction product mixture was worked up to yield 0.9 g. of an oil, which was identified as 1-(3-chlorophenyl)-2-ethyl-4-phenyl-3-pyrazolin-5-one.

|   | Theoretical | Found |
|---|---|---|
| C | 68.34% | 68.15% |
| H | 5.06 | 4.89 |
| N | 9.38 | 9.29 |

EXAMPLE 19

2-ethyl-4-phenyl-1-($\alpha,\alpha,\alpha$-trifluoro-m-tolyl)-3-pyrazolin-5-one

A mixture of 8.2 g. of the atropic acid, methyl ester, (prepared in Example 18), 8.5 g. of m-trifluoromethylphenylhydrazine hydrochloride, 100 ml. of benzene and 4 g. of triethylamine, was refluxed overnight and worked up to yield 6.5 g. of 4-phenyl-1-($\alpha,\alpha,\alpha$-trifluorom-tolyl)-3-pyrazolin-5-one having a melting point of about 210°–213° C.

A mixture of 2.2 g. of the pyrazolinone prepared above, 2 g. of potassium carbonate, 25 ml. of ethyl iodide and 25 ml. of ethanol was refluxed for about 3 hours. The reaction mixture was worked up in the usual manner to yield an oil which was identified by NMR spectrum as 2-ethyl-4-phenyl-1-($\alpha,\alpha,\alpha$-trifluoro-m-tolyl)-3-pyrazolin-5-one.

The compounds described above have been tested in a number of herbicidal test systems to determine the range of their herbicidal efficacy. The results produced by the compounds in the representative tests reported below are exemplary of the activity of the compounds.

Compound application rates are expressed in kilograms of the compound per hectare of land (kg./ha.) throughout this document.

Blank spaces in the tables below indicate that the compound was not tested against the named species. In the tests below, plants were rated on a 1–5 scale, on which 1 indicates normal plants and 5 indicates dead plants or no emergence. The compounds are identified by their example numbers.

Test 1 broad spectrum greenhouse test

Square plastic pots were filled with a sandy sterilized greenhouse soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test.

The table below reports results of testing typical compounds of the invention.

Table 1

| Compound of Example No. | Preemergence | | | Postemergence | | |
|---|---|---|---|---|---|---|
| | Tomato | Large Crabgrass | Pigweed | Tomato | Large Crabgrass | Pigweed |
| 1 | 3 | 4 | 4 | 4 | 3 | 2 |
| 2 | 5 | 5 | 5 | 5 | 5 | 5 |
| 4 | 5 | 5 | 5 | 4 | 4 | 4 |
| 5 | 4 | 5 | 5 | 5 | 5 | 5 |
| 6 | 4 | 5 | 4 | 3 | 4 | 4 |
| 7 | 3 | 4 | 4 | 5 | 3 | 5 |
| 8 | 3 | 4 | 3 | 4 | 4 | 3 |
| 9 | 2 | 5 | 5 | 2 | 3 | 3 |

Test 2 multi-species greenhouse test

The test was conducted in general like the test above. The seeds were planted in flat metal trays, rather than in pots. The compounds were formulated according to the procedure above, except that about 6 g./100 ml. of the compound was dissolved in the surfactant-containing solvent, and the organic solution was diluted with appropriate amounts of water before application to the trays. The compounds were applied at various rates which are indicated in the table below and the results of testing against the species named below are as follows. Where more than one replicate was run, the results were averaged.

| Compound of Ex. No. | Rate of Appln. kg./ha. | Corn | Cotton | Soybean | Wheat | Alfalfa | Sugar beet | Rice | Cucumber | Tomato | Barnyard Grass | Lambsquarter | Large Crabgrass | Mustard | Pigweed | Foxtail | Wild Oat | Velvetleaf | Jimsonweed | Morningglory | Zinnia |
|---|---|---|---|---|---|---|---|---|---|---|---|---|---|---|---|---|---|---|---|---|---|
| 1 | 0.56 | 1 | 1 | 1 | 2 | 1 | 1 | 1 | 1 | 1 | 2 | 4 | 4 | 2 | 2 | 2 | 2 | 1 | — | 4 | 1 |
|  | 2.2 | 2 | 1 | 1 | 3 | 1 | 2 | 1 | 1 | 1 | 5 | 5 | 5 | 5 | 3 | 3 | 2 | 2 | 3 | 4 | 2 |
|  | 9.0 | 2 | 1 | 1 | — | — | — | — | — | — | — | — | — | — | — | — | — | — | — | — | 5 |
| 2 | 1.1 | 2 | 1 | 1 | 2 | 1 | 2 | 2 | 2 | 1 | 3 | 2 | 3 | 3 | 3 | 3 | 2 | 2 | — | — | — |
| 3 | 4.5 | 2 | 1 | 1 | 4 | 2 | 4 | 2 | 2 | 3 | 5 | 4 | 5 | 4 | 5 | 4 | — | 4 | 2 | 4 | 2 |
|  | 9.0 | 4 | 1 | 2 | 3 | 2 | 4 | 2 | 3 | 3 | 4 | 4 | 5 | 4 | 4 | 5 | 3 | 4 | 3 | 4 | 5 |
| 4 | 1.1 | 2 | 1 | 1 | 2 | 2 | 2 | 1 | 2 | 2 | 3 | 5 | 5 | 4 | 4 | 4 | 2 | 2 | — | — | 1 |
|  | 9.0 | 4 | 1 | 2 | 4 | 3 | 4 | 1 | 4 | 3 | 5 | 5 | 5 | 5 | 5 | 5 | 3 | 4 | 2 | 2 | 2 |
| 5 | 1.1 | 2 | 1 | 1 | 2 | 1 | 1 | 1 | 1 | 1 | 3 | 4 | 4 | 3 | 4 | 4 | 3 | 2 | 1 | 2 | 2 |
| 6 | 4.5 | 3 | 1 | 2 | 2 | 2 | 3 | 2 | 4 | 3 | 5 | 4 | 5 | 4 | 5 | 4 | 3 | 3 | 2 | 4 | 3 |
|  | 9.0 | 2 | 1 | 1 | 2 | 1 | 1 | 1 | 1 | 2 | 2 | 2 | 4 | 2 | 4 | 4 | 2 | 2 | 2 | 2 | 2 |
| 7 | 1.1 | 2 | 1 | 1 | 2 | 1 | 2 | 1 | 1 | 2 | 3 | 5 | 5 | 4 | 4 | 4 | 3 | 3 | 2 | 3 | 3 |
|  | 4.5 | 3 | 1 | 1 | 3 | 3 | 3 | 2 | 4 | 3 | 4 | 4 | 5 | 4 | 4 | 5 | 3 | 3 | 3 | 3 | 2 |
|  | 9.0 | 2 | 1 | 1 | 2 | 1 | 2 | 2 | 5 | 2 | 2 | 2 | 4 | 2 | 3 | 3 | 2 | 2 | — | 2 | 2 |
| 8 | 1.1 | 2 | 1 | 1 | 1 | 1 | 1 | 1 | — | 1 | 2 | 4 | 4 | 3 | 4 | 4 | 2 | 2 | — | 2 | 2 |
|  | 4.5 | 4 | 1 | 2 | 2 | 2 | 2 | 2 | 4 | 3 | 4 | 4 | 5 | 4 | 5 | 5 | 4 | 4 | 4 | 4 | 3 |
|  | 9.0 | 4 | 1 | — | 3 | 5 | 5 | 3 | 3 | 4 | 4 | 5 | 5 | 5 | 5 | 5 | 4 | 5 | 4 | 4 | 4 |
| 9 | 9.0 | — | — | — | — | — | — | — | — | — | — | — | — | — | — | — | — | 2 | — | — | — |
| 10 | 2.2 | 1 | 1 | 1 | 1 | 1 | 1 | 1 | 1 | 2 | 1 | 1 | 3 | 1 | 2 | 2 | 1 | 2 | 1 | 1 | 1 |
|  | 4.5 | 2.5 | — | 1.5 | 2.5 | 3 | 3 | 1.5 | 3 | 3 | 3 | 3 | 4.5 | 2 | 2 | 4.5 | 2 | 2.5 | 1.5 | — | — |
| 11 | 2.2 | 1 | 1 | 3 | 3 | 2 | 5 | 3 | 1 | 3 | 3.5 | 4.5 | 5 | 3 | 5 | 5 | 4 | 4 | 2 | 2 | 2 |
|  | 9.0 | 3 | 1 | 3 | 4 | 5 | 5 | 2 | 2 | 3 | 5 | 5 | 5 | 5 | 5 | 5 | 4 | 4 | 2 | 2 | 2 |
| 12 | 0.28 | 2 | 1 | 1 | 2 | 2 | 3 | 1 | 1 | 1 | 3 | 2 | 4 | 2 | 4 | 3 | 3 | 2 | 2 | 2 | 2 |
|  | 0.56 | 2 | 1 | — | 2 | 3 | 3 | — | 2 | 2 | 3 | 3 | 4 | 2 | 4 | 3 | 3 | 3 | 2 | 2 | 2 |
|  | 1.1 | 2 | 1 | 1 | 2 | 3 | 3 | 1 | 1 | 2.5 | 3 | 4.5 | 5 | 3.5 | 5 | 4 | 3 | 3 | 2 | 3 | 3 |
|  | 2.2 | 2.5 | 2 | 2 | 2.5 | 2.5 | 3 | 1 | 2 | 3 | 4 | 5 | 5 | 4 | 5 | 5 | 3 | 4 | 2.5 | 2.5 | 2 |
|  | 4.5 | 3 | 1 | 2 | 3 | 4 | 5 | 2 | 2 | 3 | 5 | 4 | 5 | 4 | 5 | 5 | 4 | 4 | 3 | 3 | 3 |
|  | 9.0 | 3 | 1 | 2 | 3 | 5 | 5 | 2 | 3 | 3 | 4 | 5 | 5 | 5 | 5 | 5 | 4 | 4 | 3 | 4 | 3 |
| 13 | 0.28 | 2 | 1 | — | 2 | 2 | 3 | 1 | 2 | 1 | 3 | 2 | 4 | 2 | 4 | 3 | 3 | 2 | 2 | 2 | 2 |
|  | 0.56 | 2 | 1 | — | 2 | 3 | 3 | — | 2 | 2 | 3 | 3 | 4 | 3 | 4 | 4 | 3 | 3 | 2 | 2 | 2 |
|  | 1.1 | 2.5 | 1.5 | 1 | 2 | 3 | 4 | 1 | 1.5 | 2.5 | 3.5 | 4.5 | 5 | 4.5 | 5 | 5 | 3 | 3.5 | 3 | 3 | 2 |
|  | 2.2 | 2 | 1 | — | 2 | 3 | 4 | — | 1 | 3 | 4 | 5 | 4 | 5 | 5 | 4 | 3 | 3 | 2.5 | 2 | 2 |
|  | 4.5 | 2 | 1 | — | 2 | 3 | 3 | — | 1 | 3 | 4 | 4 | 4 | 4 | 4 | 4 | 3 | 3 | 3 | 3 | 2 |
|  | 9.0 | 3 | 2 | — | 3 | 4 | 4 | 2 | 3 | 3 | 4 | 5 | 4 | 4 | 5 | 5 | 3 | 3 | 3 | 3 | 2 |
| 14 | 0.28 | 2 | 2 | 1 | 2 | 2 | 3 | 2 | 1 | 2 | 2 | 3 | 4 | 2 | 4 | 3 | 4 | 3 | 2 | 2 | 2 |
|  | 0.56 | 2 | 2 | 1 | 2 | 2 | 4 | 2 | 3 | 2 | 3 | 4 | 4 | 2 | 5 | 4 | 3 | 3 | 2 | 3 | 2 |
|  | 1.1 | 2 | 1 | — | 2 | 2 | 4 | 2 | 3 | 3 | 4 | 3 | 4 | 3 | 5 | 4 | 3 | 3 | 3 | 3 | 2 |
|  | 2.2 | 3 | 1 | 2 | 3 | 3 | 4 | 2 | 3 | 3 | 4 | 5 | 4 | 4 | 5 | 5 | 3 | 4 | 3 | 4 | 3 |
|  | 4.5 | 3 | 2 | 2 | 3 | — | 4 | 2 | 3 | 3 | 4 | 5 | 5 | 4 | 5 | 4 | 3 | 4 | 3 | 4 | 3 |
|  | 9.0 | 3 | 2 | 2 | 3 | 3 | 4 | 2 | 3 | 3 | 5 | 5 | 5 | 4 | 5 | 5 | — | 4 | 3 | 3 | 3 |
| 15 | 0.07 | 2 | 1 | 1 | 1 | 1 | 2 | 1 | 1 | 1 | 2 | 3 | 4 | 2 | 3 | 4 | — | 1 | 1 | 1 | 1 |
|  | 0.14 | 2.5 | 1 | — | 2 | 2 | 4 | 2 | 1 | 2 | 2.5 | 4.5 | 4 | 3 | 5 | 5 | 2.5 | 3 | 2 | 2 | 2 |
|  | 0.28 | 2.5 | 2 | 1.5 | 2 | 2.5 | 3 | 2.5 | 3 | 3 | 3.5 | 5 | 4 | 4.5 | 5 | 4 | 2 | 3 | 3 | 3 | 3 |
|  | 0.56 | 3 | 2 | — | 4 | 3 | 5 | 3 | 3 | 5 | 5 | 5 | 5 | 5 | 5 | 5 | 3 | 4 | 3 | 3 | 3 |
|  | 1.1 | 3.5 | 2 | 2 | 3.5 | 4 | 5 | 5 | 3 | 4 | 5 | 5 | 5 | 5 | 5 | 5 | 3 | 4 | 4 | 4 | 3 |
|  | 2.2 | 4 | 2 | 2 | 4 | 4 | 4 | 3 | 3 | 4 | 5 | 5 | 5 | 5 | 5 | 5 | 3 | 4 | 5 | 4 | 3 |
|  | 4.5 | 4 | — | 2 | 4 | 4 | 5 | 5 | 3 | 4 | 4 | 5 | 5 | 4.5 | 5 | 4 | 4 | 4 | 4 | 3 | 3 |
|  | 9.0 | 4 | 1 | 4 | 4 | 4 | 4 | 3 | 3 | 4 | 5 | 5 | 5 | 5 | 5 | 5 | 3 | 4 | 3 | 4 | 2 |
| 15 | 0.07 | 1 | 1 | 1 | 1 | 1 | 2 | 1 | 1 | 1 | 2 | 2 | 2 | 2 | 2 | 1 | 1 | 1 | 1 | 1 | 1 |
|  | 0.14 | 1.5 | 1 | 1 | 2 | 2 | 2 | 2 | 1 | 2 | 2 | 3 | 4 | 2.5 | 2.5 | 3 | 2 | 2.5 | 1.5 | 1.5 | 1.5 |
| 16 | 0.28 | 1.5 | 1 | 1 | 2 | 2 | 2 | 1.5 | 1 | 2 | 3.5 | 3.5 | 4.5 | 2.5 | 2.5 | 4.5 | 1.5 | 2.5 | 1.5 | 1.5 | 1.5 |
|  | 0.56 | 2 | 1 | 1 | 2 | 3 | 3 | 1 | 1 | 2 | 4 | 4 | 5 | 3 | 3 | 5 | 2 | 2 | 1 | 1 | 2 |

-continued

Preemergence

| Compound of Ex. No. | Rate of Appln. kg/ha | Corn | Cotton | Soybean | Wheat | Alfalfa | Sugar beet | Rice | Cucumber | Tomato | Barnyard Grass | Lambsquarter | Large Crabgrass | Mustard | Pigweed | Foxtail | Wild Oat | Velvetleaf | Jimsonweed | Morningglory | Zinnia |
|---|---|---|---|---|---|---|---|---|---|---|---|---|---|---|---|---|---|---|---|---|---|
|  | 1.1 | 2.5 | 1 | 2 | 3 | 3 | 4 | 1.5 | 2.5 | 3.5 | 4 | 3 | 4.5 | 3 | 4 | 5 | 2.5 | 2.5 | 2.5 | 2 | 2 |
|  | 2.2 | 3 | 1 | 2 | 4 | 3 | 5 | 2 | 2 | 3 | 4 | 4 | 5 | 4 | 5 | 5 | 3 | 4 | 3 | 4 | 3 |
|  | 4.5 | 4 | 2 | 3 | 4 | 3 | 5 | 3 | 4 | 4 | 4 | 4 | 5 | 4 | 5 | 5 | 3 | 4 | 3 | 4 | 3 |
| 17 | 9.0 | 4 |  |  |  |  |  |  |  |  |  |  |  |  |  |  |  |  |  |  | 4 |
|  | 1.1 | 2 | 1 | 1 | 2 | 1 | 2 | 1 | 1 | 1 | 3 | 3 | 4 | 2 | 3 | 3 | 2 | 2 | 1 | 3 | 1 |
|  | 2.2 | 2 | 1 | 1 | 2 | 2 | 4 | 1 | 2 | 1 | 4 | 3 | 4 | 3 | 3 | 4 | 2 | 2 | 2 | 2 | 2 |
|  | 4.5 | 2 | 1 | 1 | 3 | 2 | 2 | 1 | 2 | 2 | 4 | 4 | 5 | 3 | 4 | 4 | 3 | 4 | 2 | 3 | 2 |
|  | 9.0 | 3 |  |  |  |  |  |  |  |  |  |  |  |  |  |  |  |  |  |  | 4 |
|  | 0.28 | 2 | 1 |  | 2 | 1 | 3 | 1 | 1 | 2 | 2 | 3 | 4 | 1 | 5 | 3 | 1 | 1 | 1 | 2 | 1 |
|  | 0.56 | 2 | 1 | 1 | 2 | 2 | 4 | 1 | 1 | 3 | 3 | 4 | 4 | 1 | 2 | 5 | 2 | 2 | 2 | 3 | 2 |
|  | 1.1 | 3 | 1.5 | 2 | 2.5 | 3 | 4 | 1.5 | 2 | 2 | 4 | 4 | 4.5 | 3 | 3.5 | 5 | 3 | 3 | 1.5 | 2.5 | 1 |
| 18 | 2.2 | 4 | 1 | 1 | 3 | 4 | 5 | 1 | 1 | 1 | 4 | 5 | 5 |  | 5 | 5 |  | 4 | 2 | 4 | 2 |
|  | 4.5 | 4 | 2 | 3 | 4 | 5 | 5 | 3 | 3 | 5 | 5 | 5 | 5 | 4 | 5 | 4 | 3 | 5 |  | 4 | 4 |
|  | 9.0 | 4 |  |  |  |  |  |  |  |  |  |  |  | 5 |  |  |  |  |  |  | 2 |
|  | 1.1 | 3 | 1 | 1 | 2 | 2 | 3 | 1 | 1 | 2 | 2 | 4 | 5 | 3 | 5 | 5 | 2 | 2 | 1 | 3 | 1 |
|  | 2.2 | 2 | 1 | 1 | 2 | 2 | 2 | 2 | 1 | 2 | 3 | 4 | 5 | 4 | 3 | 5 | 2 | 3 | 2 | 1 | 1 |
| 19 | 4.5 | 3 | 2 | 1 | 3 | 5 | 5 | 2 | 1 | 3 | 4 | 5 | 5 | 3 | 5 | 5 | 2 | 3 | 2 | 3 | 2 |
|  | 9.0 | 3 |  |  |  |  |  |  |  |  |  |  |  |  |  |  |  | 3 |  | 4 | 2 |

| Compound of Example No. | Rate of Appln. kg./ha. | Postemergence | | | | | | |
|---|---|---|---|---|---|---|---|---|
| | | Corn | Large Crabgrass | Pigweed | Foxtail | Velvetleaf | Morning-glory | Zinnia |
| 2 | 9.0 | 2 | 3 | 2 | 2 | 2 | 3 | 3 |
| 4 | 9.0 | 2 | 4 | 3 | 3 | 3 | 2 | 2 |
| 5 | 9.0 | 2 | 2 | 2 | 1 | 1 | 1 | 1 |
| 6 | 9.0 | 1 | 2 | 2 | 1 | 1 | 1 | 1 |
| 7 | 9.0 | 2 | 4 | 4 | 3 | 3 | 3 | 3 |
| 8 | 9.0 | 1 | 4 | 3 | 2 | 2 | 2 | 2 |
| 9 | 9.0 | 2 | 2 | 3 | 1 | 1 | 2 | 2 |
| 11 | 9.0 | 4 | 3 | 2 | 3 | 2 | 2 | 2 |
| 13 | 9.0 | 2 | 2 | 2 | 2 | 2 | 2 | 2 |
| 14 | 9.0 | 3 | 3 | 2 | 3 | 2 | 2 | 2 |
| 15 | 9.0 | 3 | 3 | 2 | 3 | 2 | 2 | 2 |
| 16 | 9.0 | 2 | 3 | 3 | 3 | 3 | 2 | 2 |
| 17 | 9.0 | 2 | 2 | 2 | 2 | 2 | 2 | 2 |
| 18 | 9.0 | 2 | 2 | 2 | 2 | 2 | 2 | 2 |

Test 3 resistant weed tests

Typical compounds were evaluated in a test system which determined their ability to reduce the vigor of weeds which are resistant to many herbicides. The compounds were formulated and dispersed, and the dispersions were applied, as described in Test 1 above. The application rate was 9.0 kg./ha. in all of the tests reported here.

| Compound of Ex. No. | Preemergence | | | | Postemergence |
|---|---|---|---|---|---|
| | Yellow Nutsedge | Night-shade | Sickle-pod | Rag-weed | Yellow Nutsedge |
| 1 | 1 | 4 | 2 | 4 | 2 |
| 4 | 4 | 5 | 4 | 4 | 4 |
| 5 | 2 | 5 | 3 | 2 | 1 |
| 6 | 4 | 4 | 2 | 4 | 2 |
| 7 | 4 | 4 | 2 | 3 | 2 |
| 8 | 3 | 4 | 2 | 3 | 1 |

The broad spectrum activity of the compounds of this invention is illustrated by the above examples. The test results point up the efficacy of the compounds against annual grasses, the relatively easily-controlled broadleaves such as pigweed, and the more resistant broadleaves such as nightshades. Plant scientists will recognize that the exemplified activity of the compounds shows that they are broadly effective against unwanted herbaceous plants, which will be referred to as weeds, for the sake of brevity.

As the above test results demonstrate, the compounds are used to reduce the vigor of weeds by contacting them with an herbicidally-effective amount of one of the compounds. The term "reduce the vigor of" is used to refer to both killing and injuring the weed which is contacted with a compound. In some instances, as is clear from the test results, the whole population of the contacted weed is killed. In other instances, part of the weeds are killed and part of them are injured, and in still other instances, none of the weeds are killed but are merely injured by application of the compound. It will be understood that reducing the vigor of the weed population by injuring part of them is beneficial, even though part of the population survives application of the compound. The weeds, the vigor of which has been reduced, are unusually susceptible to the stresses which normally afflict plants, such as disease, drought, lack of nutrients and so forth.

Thus, the treated weeds are likely to expire due to stress of the environment, even though they survive application of the compound. Further, if the treated weeds are growing in cropland, the crop, as it grows normally, tends to shade out the treated weeds of reduced vigor. Therefore, the crop has a great advantage over the treated weeds in the competition for nutrients and sunlight. Still further, when the treated weeds are growing in fallow land, or industrial property which is desired to be bare, the reducting in their vigor necessarily tends to minimize the treated weeds' consumption of water and nutrients, and also minimizes the fire hazard and nuisance which the weeds present.

The compounds are herbicidally effective when applied both preemergence and postemergence. Thus, they can be used both by direct contact of the compounds with emerged weeds, and by applying the compounds to the soil, where they come into contact with germinating and emerging weeds. Preemergence application of the compounds, wherein the germinating and emerging weeds are contacted with the compound through soil application, is preferred.

Accordingly, an important embodiment of this invention is a method of reducing the vigor of weeds which comprises contacting the weeds with an herbicidally-effective amount of a compound of the invention. The term herbicidally-effective amount refers to an amount which will reduce the vigor of the treated weed. In the context of this invention, weed seeds, which are contacted with the compounds by application of the compounds to the soil, are regarded as weeds.

Amounts of herbicides are measured in terms of the weight of herbicide applied per unit area, usually called the application rate. The best application rate of a given compound of the invention for the control of a given weed varies, of course, depending upon the climate, soil texture, water and organic matter contents of the soil and other factors known to those skilled in plant science. It will be found, however, that the optimum application rate is usually in the range from about 0.5 to about 20 kg./ha.

It is not implied, of course, that all compounds of this invention are effective against all weeds at all rates. Some compounds are more effective against some types of weeds, other compounds are more effective against other types. All of the compounds, however, are effective against at least some weeds. It is within the ordinary skill of a plant scientist to ascertain the weeds which are most advantageously controlled with the various compounds, and the best application rate for the particular use.

The compounds are applied to the soil or to emerged weeds in the manners usual in agriculture. It is best to apply the compounds in the form of the herbicidal compositions which are important embodiments of the present invention. They may be applied to the soil in the form of either water-dispersed or granular compositions, the preparation of which will be discussed below. Usually, water-dispersed compositions will be used for the application of the compounds to emerged weeds. The compositions are applied with any of the many types of sprayers and granular applicators which are in wide use for the distribution of agricultural chemicals over soil or standing vegetation. In general, the compositions are formulated in the manners usual in agricultural chemistry.

Very often, the compounds are formulated as concentrated compositions which are applied either to the soil or the foilage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier, and surfactants. The concentration of the compound is usually from about 10 percent to about 90 percent. The inert carrier is usually chosen from among the attapulgite clays, the montmorillonite clays, the kaolin clays, the diatomaceous earths and the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable.

We claim:
1. A compound of the formula

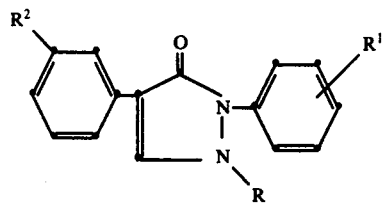

wherein
R represents $C_1$–$C_3$ alkyl;
$R^1$ and $R^2$ independently represent hydrogen, chloro, fluoro, bromo, methyl or trifluoromethyl, provided that $R^1$ and $R^2$ do not simultaneously represent hydrogen; and provided that $R^1$ may not be bromo or chloro in the 4-position.

2. A compound as in claim 1 wherein
R represents $C_1$–$C_2$ alkyl;
$R^1$ represents hydrogen, chloro, or fluoro; provided that $R^1$ may not be chloro in the 4-position; and
$R^2$ represents trifluoromethyl.

3. The compound of claim 1 which is 2-methyl-1-phenyl-4-(α,α,α-trifluoro-m-tolyl)-3-pyrazolin-5-one.

4. The compound of claim 1 which is 2-ethyl-1-phenyl-4-(α,α,α-trifluoro-m-tolyl)-3-pyrazolin-5-one.

5. The compound of claim 1 which is 2-methyl-1-(4-fluorophenyl)-4-(α,α,α-trifluoro-m-tolyl)-3-pyrazolin-5-one.

6. The compound of claim 1 which is 2-methyl-1-(3-chlorophenyl)-4-(α,α,α-trifluoro-m-tolyl)-3-pyrazolin-5-one.

7. The compound of claim 1 which is 2-methyl-1-(2-chlorophenyl)-4-(α,α,α-trifluoro-m-tolyl)-3-pyrazolin-5-one.

8. The compound of claim 1 which is 2-ethyl-1-(3-chlorophenyl)-4-(α,α,α-trifluoro-m-tolyl)-3-pyrazolin-5-one.

9. The compound of claim 1 which is 1-(3-bromophenyl)-2-ethyl-4-(α,α,α-trifluoro-m-tolyl)-3-pyrazolin-5-one.

10. The compound of claim 1 which is 2-ethyl-1-(4-fluorophenyl)-4-(α,α,α-trifluoro-m-tolyl)-3-pyrazolin-5-one.

11. The compound of claim 1 which is 1,4-bis(3-chlorophenyl)-2-ethyl-3-pyrazolin-5-one.

* * * * *

UNITED STATES PATENT OFFICE
CERTIFICATE OF CORRECTION

Patent No. 4,118,574      Dated October 3, 1978

Inventor(s) James Richard Beck & Robert Peter Gajewski

It is certified that error appears in the above-identified patent and that said Letters Patent are hereby corrected as shown below:

Column 15, Compound 18, kg./ha. 2.2, Heading "Pigweed":
    Insert --3--.

Column 17, line 39:    "inventiion" should read --invention--.

Column 18, line 25:    "reducting" should read --reduction--.

Column 19, line 17:    "foilage" should read --foliage--.

Signed and Sealed this

Eighth Day of May 1979

[SEAL]

Attest:

RUTH C. MASON
*Attesting Officer*

DONALD W. BANNER
*Commissioner of Patents and Trademarks*